(12) United States Patent
Talavera-Peraza

(10) Patent No.: US 9,387,060 B2
(45) Date of Patent: Jul. 12, 2016

(54) GAUZE PAD HOLDER FOR POST-SURGICAL INTRAORAL USE

(71) Applicant: Cesar R Talavera-Peraza, Hatillo, PR (US)

(72) Inventor: Cesar R Talavera-Peraza, Hatillo, PR (US)

( * ) Notice: Subject to any disclaimer, the term of this patent is extended or adjusted under 35 U.S.C. 154(b) by 115 days.

(21) Appl. No.: 14/189,994

(22) Filed: Feb. 25, 2014

(65) Prior Publication Data

US 2015/0238295 A1      Aug. 27, 2015

(51) Int. Cl.
*A61C 19/00* (2006.01)

(52) U.S. Cl.
CPC .................... *A61C 19/001* (2013.01)

(58) Field of Classification Search
CPC ...................................... A61C 19/001
USPC ................................. 433/136, 138
See application file for complete search history.

(56) References Cited

U.S. PATENT DOCUMENTS

| 824,087 | A | * | 6/1906 | Babcock | A46B 3/18 |
| | | | | | 15/167.1 |
| 938,421 | A | * | 10/1909 | Hakins | 15/244.1 |
| 1,010,147 | A | * | 11/1911 | Ivory | 433/138 |
| 2,885,783 | A | * | 5/1959 | Golden | 433/139 |
| 2,897,597 | A | * | 8/1959 | Ivory | 433/138 |
| 3,267,512 | A | * | 8/1966 | Wiley | 401/201 |
| 5,774,925 | A | * | 7/1998 | Pryor, III | 15/244.1 |
| 5,817,121 | A | * | 10/1998 | Christoudias | 606/190 |

* cited by examiner

*Primary Examiner* — Ralph Lewis
(74) *Attorney, Agent, or Firm* — Hector M. Reyes Rivera

(57) ABSTRACT

A holder for safely securing a gauze pad for use in a post-surgical area in the intraoral cavity of a patient in order to allow a blood clot to form in safe, hygienic and sanitary conditions. The holder provides a holding cavity wherein the gauze pad is secured and held. It also requires a handle section that allows the external control of the gauze pad by the patient. Embodiments having holding sections with different ergonomic shapes according to the particular position of the intraoral surgical area requiring placement of the gauze pad are described.

6 Claims, 7 Drawing Sheets

GAUZE PAD HOLDER FOR POST-SURGICAL INTRAORAL USE

TECHNICAL FIELD OF THE INVENTION

This invention relates to gauze pad holders. More particular, the invention is directed to gauze pad holders useful in securing and holding a gauze pad at a particular area of the mouth after a surgical procedure has been performed in the intraoral cavity.

BACKGROUND OF THE INVENTION

Surgical procedures inside the mouth, such as tooth extractions, generally cause more bleeding than a skin wound due to the difficulty associated with the process of drying out the gums and thus retardation of the blood clot formation. In order to control the bleeding after the intraoral surgical procedure is performed; a common practice is to place a gauze pad over the dental extraction site and bite on it for about 30 minutes, so that pressure is applied to surgical area in order to maintain a dry field an allow a blood clot to form.

Said procedure has a series of disadvantages. For instance, said gauze pad is usually inserted in the postsurgical intraoral area by healthcare personnel, personal assistants or by the patient himself, generally by introducing their hands into the mouth. This represents a poor hygienic practice that exposes the surgical area to potential pathogens such as bacteria, increasing the chances of opportunistic infections and other postsurgical complications. Indeed, presently, infections involving antibiotic resistant bacteria are a real challenge to treat, thus new preventive measures with the aim of avoiding exposure of such bacteria are an essential part of the standard of care process.

Another potentially dangerous situation is due to the fact that the gauze pad is not secured by any means inside the oral cavity of a patient who is generally under some kind of sedation, said gauze pad may be displaced from the surgical area to the patient's pharynx, causing an obstruction of the patient's airway; thus representing and asphyxiation or choking hazard.

Furthermore, since the patient has no direct visual contact of the surgical site's exact location, there is a high chance that he or she may not be able to place and maintain the gauze pad in the proper location, thus the effect of applying pressure over the desired and specific intraoral area may not be achieved. In a similar manner, after using said gauze pad, it is uncomfortable and unpleasant to remove it from the mouth, since it is soaked with blood and saliva. Furthermore, in order for the gauze pad to be effective in the postsurgical intraoral area, the gauzes should be folded properly in a square shape by folding the gauzes in half twice so that the resulting gauze pad is ideal for the placement over the extraction site. Therefore, there is a need to provide a suitable hygienic and sanitary gauze pad holder that allows the control of a gauze pad over a particular and specific postsurgical intraoral area.

OBJECTS AND SUMMARY OF THE INVENTION

It is an object of the invention to provide a gauze pad holder that allows placing gauze pads properly in a post-surgical intraoral area in safe, hygienic and sanitary conditions. It is another object of the invention to provide a preventive measure with the aim of avoiding exposure of antibiotic resistant bacteria during and after intraoral surgical procedures. Another object of the invention is to provide a gauze pad holder that eliminates the need of using direct hand contact in order to properly place said gauze pad in the oral cavity of a patient. Another object of the invention is to provide a gauze pad holder that allows maintaining said gauze pad over the post-surgical intraoral area providing a safe positioning that avoids the gauze pad displacement from said particular area in order to increase the effectiveness of the gauze pad in stopping the gums bleeding and avoiding potential choking of the patient caused by said gauze pad. Yet another object of the invention is to provide a gauze pad holder that allows external patient control of the pad by the patient, eliminating the need of inserting fingers in the patient's oral cavity to re-accommodate said pad, thus providing a sense of security and comfort to the patient. Another object of the invention is to provide a gauze pad holder that allows maintaining the proper folding and shape of the pad during the process that said pad is used in order to ensure ideal contact of said pad over the surgical site. Yet another object of the invention is to provide a gauze pad holder with an extra holding mechanism of securing the gauze pad in place by providing toothed elements that are inserted through the gauze pad fibers. Still another object of the invention is to provide a gauze pad holder that is ergonomically designed in order to be comfortably positioned over a post-surgical intraoral area according to the nature and surroundings of said intraoral area. Thus, embodiments having different shapes are presented, preferably to be used in molar or premolar positions. In yet another object of the invention is to provide a gauze pad holder for intraoral use that is easy to be removed or substituted after being used without the need of inserting fingers into the oral cavity. In yet another object of the invention is to provide an already disinfected, sanitary gauze pad in its proper individual holder, ready to be used in safe, hygienic and sanitary conditions.

BRIEF DESCRIPTION OF THE DRAWINGS

The foregoing and additional features and characteristics of the present invention will become more apparent from the following detailed description considered with reference to the accompanying drawings, wherein.

DETAILED DESCRIPTION OF THE EMBODIMENTS

The following detailed description illustrates the invention and a variety of embodiments by way of example and is not limited to the particular limitations presented herein as principles of the invention. This description is directed to enable one skilled in the art to make and use the invention by describing embodiments, adaptations, variations and alternatives of the invention. Any potential variations of the limitations herein described are within the scope of the invention.

In general terms, the instant invention is directed to a gauze pad holder, useful in holding a gauze pad, which is intended to be pressed or bitten in a post-surgical precise location inside the mouth, just after a surgical dental procedure has been performed. Thus, a section of the holder has been intended to be used intraoral and for instance, after tooth extraction. The instant invention comprises different embodiments able to adapt to the particular intraoral postsurgical location due to the curvature of the oral cavity and different elements may be included to further secure said gauze pad firmly in a particular mouth area after a surgical procedure.

Figure 1:
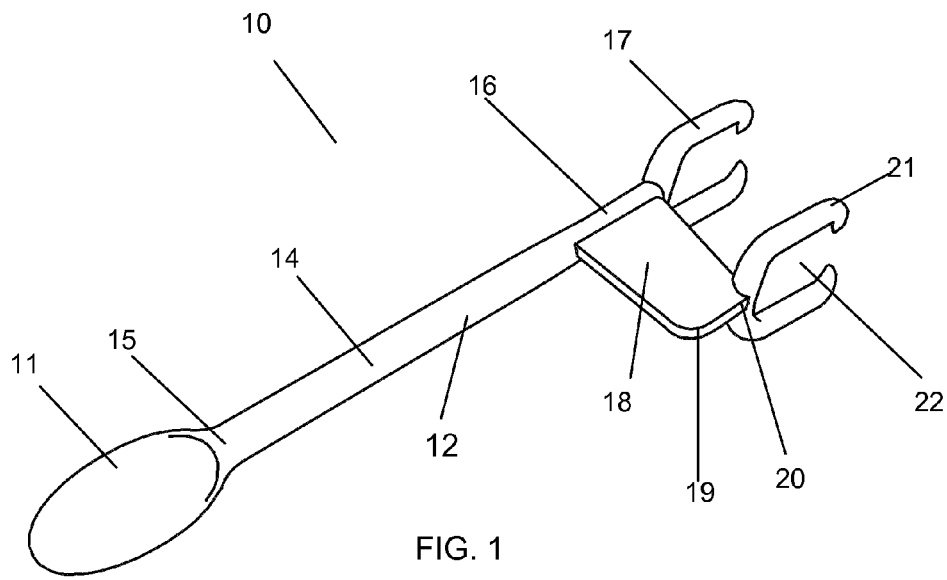
FIG. 1 shows a diagrammatical representation in a perspective view of one embodiment of the gauze pad holder according to the invention.
Figure 2:
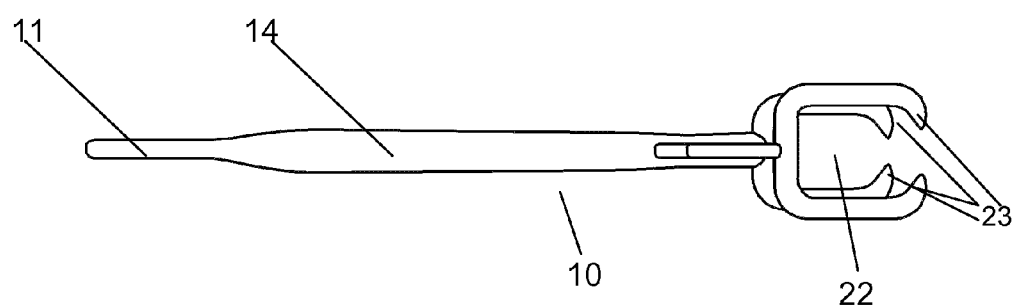
FIG. 2 illustrates a diagrammatical representation in a frontal view of the embodiment according to the invention showed in FIG. 1.
Figure 3:
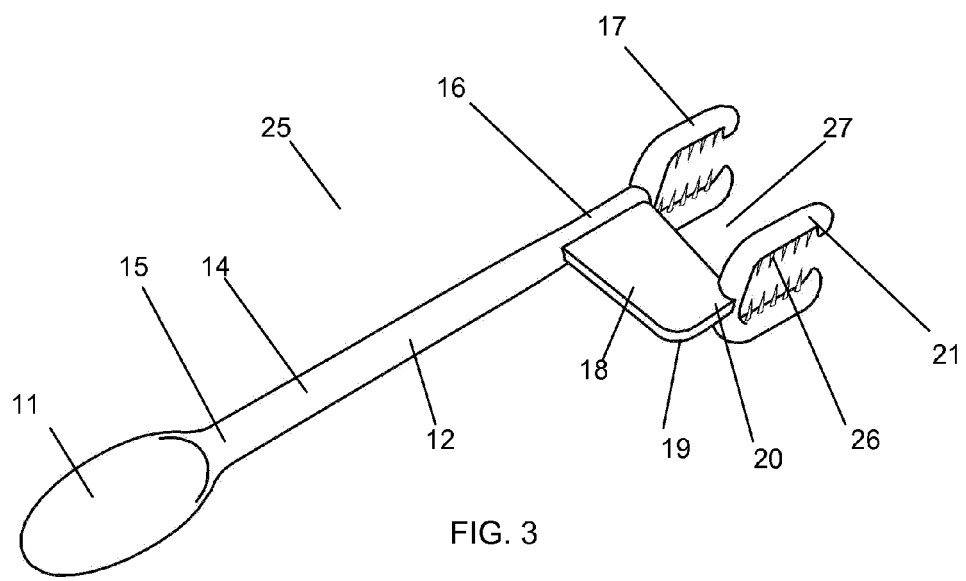
FIG. 3 illustrates a diagrammatical representation, in a perspective view of one of the gauze pad holder embodiments according to the invention.
Figure 4:
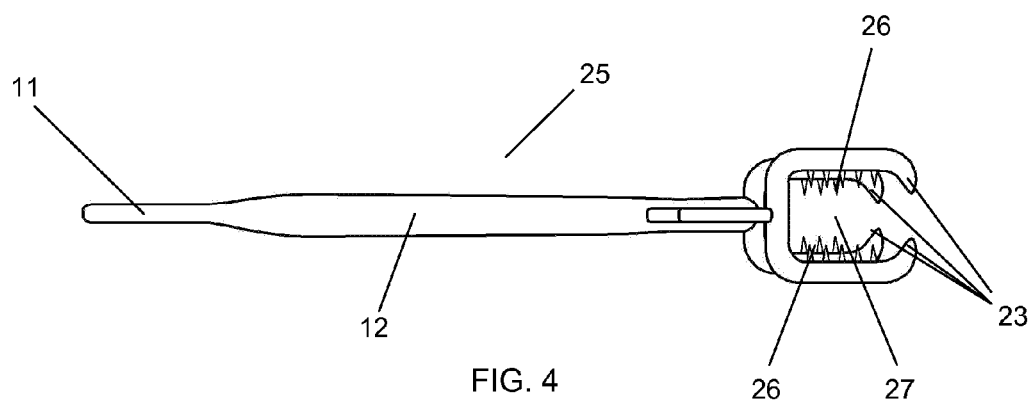
FIG. 4 illustrates a diagrammatical representation in a frontal view of the embodiment according to the invention showed in FIG. 3.

The first embodiment of the invention 10 is illustrated in FIGS. 1 and 2. A second embodiment of the invention 25 is illustrated in FIGS. 3 and 4. Embodiments 10 and 25 are very similar, as explained below and are intended to be used in any tooth extraction process, but are particularly more convenient to be used after molar and premolar extractions at the intraoral cavity.

FIG. 1 illustrates a perspective view of embodiment 10 while FIG. 2 illustrates a frontal view of said embodiment 10. It comprises a handle 11, which is illustrated having a preferably flat, oval shape with a concave center surrounded by round edges; although it may have any other suitable shape. Extending from handle 11, there is connecting unit 12, which has an elongated body 14, having a preferably cylindrical shape. It has a first end 15, wherein it is connected to handle 11 and a second end 16, wherein it is connected to a first C-shaped holding unit 17, which since it is connected at such end 16 is thus aligned or substantially aligned to handle 11.

Figure 8:
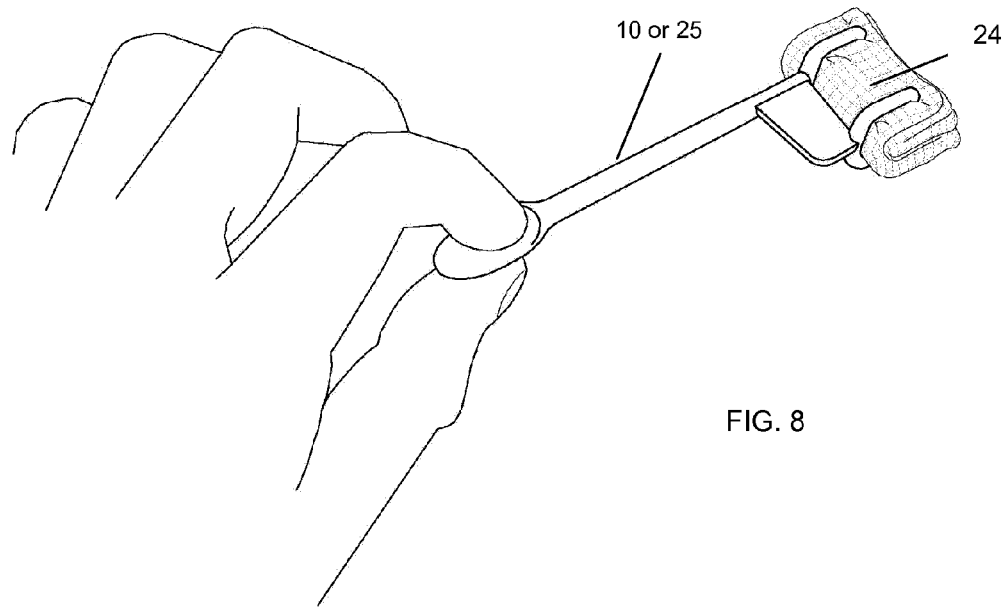
FIG. 8 shows a diagrammatical representation in perspective view of the embodiment types illustrated in FIG. 1 or FIG. 3 holding a gauze pad.

Embodiment 10 also comprises a flat supporting section 18, which is connected to and extending outwardly from the right side near said second end 16 of the connecting unit 12. Flat supporting section 18 preferably has a rectangular or near rectangular shape having the back right corner 19 preferably round and a thin width without having any sharp edges. It also comprises a front right corner 20 wherein a second C-shaped holding unit 21 is connected. Said second holding unit 21 is located in a parallel position to the first C-shaped holding unit 17. In this manner, first C-shaped holding unit 17 and second C-shaped holding unit 21 creates cavity 22, wherein a set of gauze pad 23 may be securely held, as illustrated in FIG. 8. Said first and second C-shaped holding units 17 and 21 are preferably identical in shape and size and their bodies are preferably cylindrical having its ends 23 pointing to near the interior of cavity 22, as illustrated in FIG. 2.

A second embodiment 25 according to the invention is illustrated in FIGS. 3 and 4. FIG. 3 illustrates a perspective view while FIG. 4 illustrates a frontal view of embodiment 25. The difference between embodiment 10 and embodiment 25 is that embodiment 25 comprises a series of multiple sharp pointed projections 26, coming from the top and bottom internal surface of each of the first and second holding units 17 and 21, respectively, to the interior of said C-shaped structures simulating teeth; thus providing or creating cavity 27 as a toothed cavity. Projections 26 provides an additional support to a gauze pad 24, since such projections 26 impale the fibers of the gauze pad 24, providing an extra secure holding to said gauze pad 24.

Figure 5:
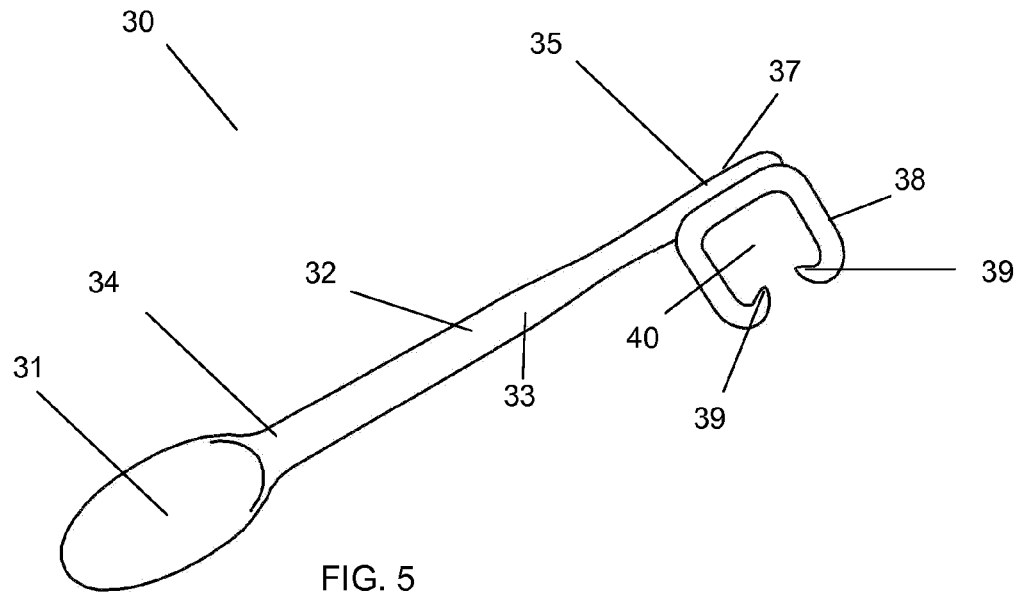
FIG. 5 and FIG. 6 show a diagrammatical representation in a perspective view of two other embodiments of the gauze holder according to the invention.
Figure 6:
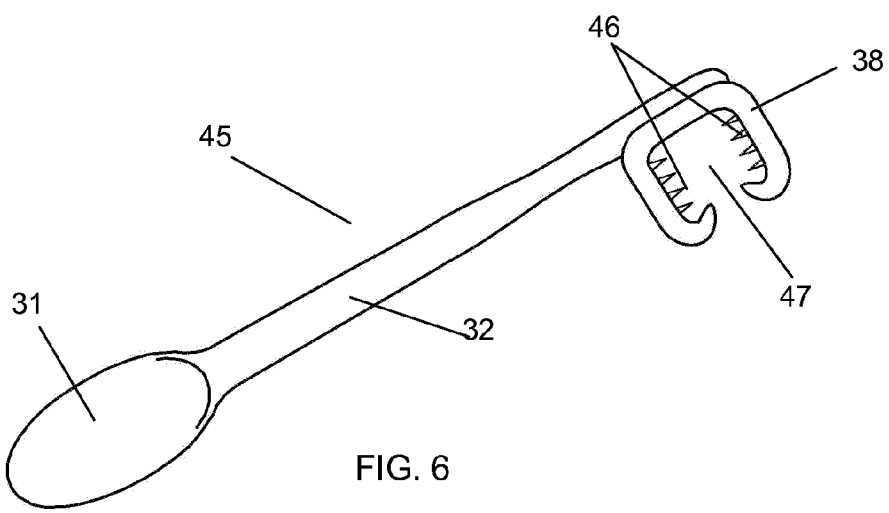
Figure 7:
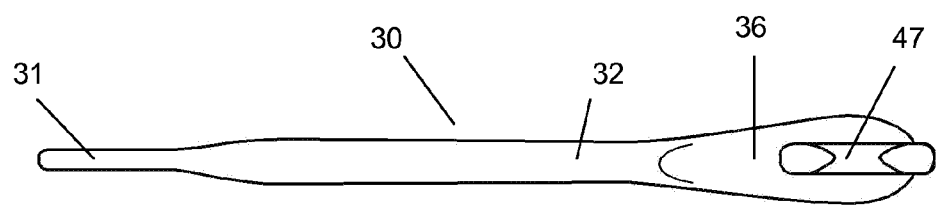
FIG. 7 illustrates a diagrammatical representation in a frontal view of any of the embodiment according to the invention already showed in FIG. 5 or 6.
Figure 9:
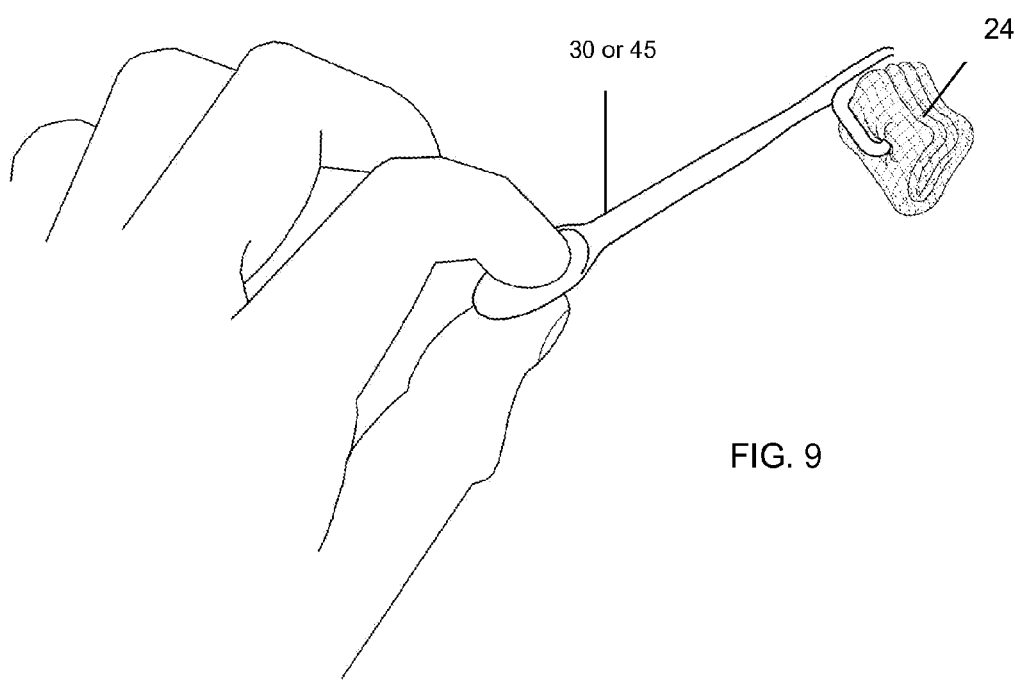
FIG. 9 shows a diagrammatical representation in perspective view of the embodiment types illustrated in FIG. 5 or FIG. 6 holding a gauze pad.

The instant invention also comprises embodiments 30 and 45, which are illustrated diagrammatically in a perspective view in FIGS. 5 and 6. Embodiment 30, illustrated in FIG. 5 comprises handle section 31 preferably having a flat, oval shape with a concave center surrounded by round edges even though it may have any other suitable shape. Extending from handle 31, there is connecting unit 32, which has an elongated body 33, having a preferably cylindrical shape. It has a first end 34, wherein it is connected to handle 31 and a second end 35 having a flat round shape comprising a lower surface 36 and an upper surface 37. On said lower surface 36 is connected a C-shaped holding unit 38, which, since it is connected at such lower surface 36 of second end 35, being thus aligned or substantially aligned to handle 31. Main body of the C-shaped structure 38 is preferably cylindrical and has its ends 39 pointing inwardly to the interior space 40 of said C-shaped holding unit 38 as illustrated in FIG. 5. Said internal space 40 is suitable to hold and firmly secure a set of gauze pad 24 as illustrated in FIG. 9.

On the other hand, the instant invention also comprises embodiment 45 which is illustrated in FIG. 6 as a perspective view. It is similar to embodiment 30 however it comprises a series of multiple sharp pointed projections 46, coming from the top and bottom internal surface of the interior of said C-shaped holding unit 38 which simulate teeth; thus providing or creating cavity 47 as a toothed cavity. As previously indicated for embodiment 25, projections 46 as in the case of projections 26 provides an additional support to a gauze pad 24, since such projections 46 impale the fibers of the gauze pad 24, providing an extra secure holding to said gauze pad 24, as illustrated in FIG. 9.

The herein disclosed embodiments may be made of any suitable strong material, such as plastic, foam, or noncorrosive metal, preferably plastic via suitable known in the art molding techniques. Even more preferably such embodiments may be made of plastic or noncorrosive metal. It is contemplated that the embodiments may have different sizes since the holder may be used in patients of different ages. It is contemplated that the herein disclosed holder may be for disposable use or alternatively, it may be for non-disposable use after being properly disinfected or sterilized.

Figure 10:
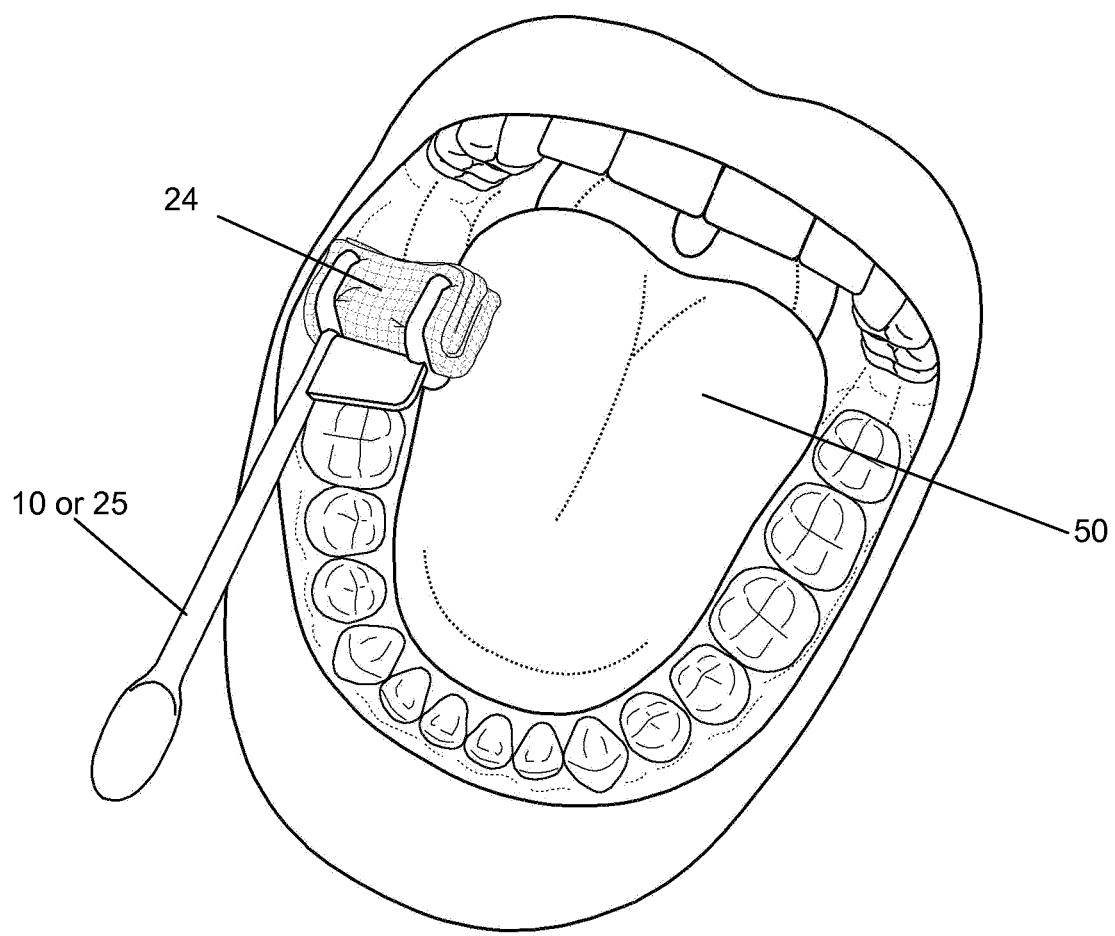
FIG. 10 shows a diagrammatical representation in perspective view of the post-surgical use of the embodiment types of the gauze pad holder illustrated in FIG. 1 or FIG. 3.
Figure 11:
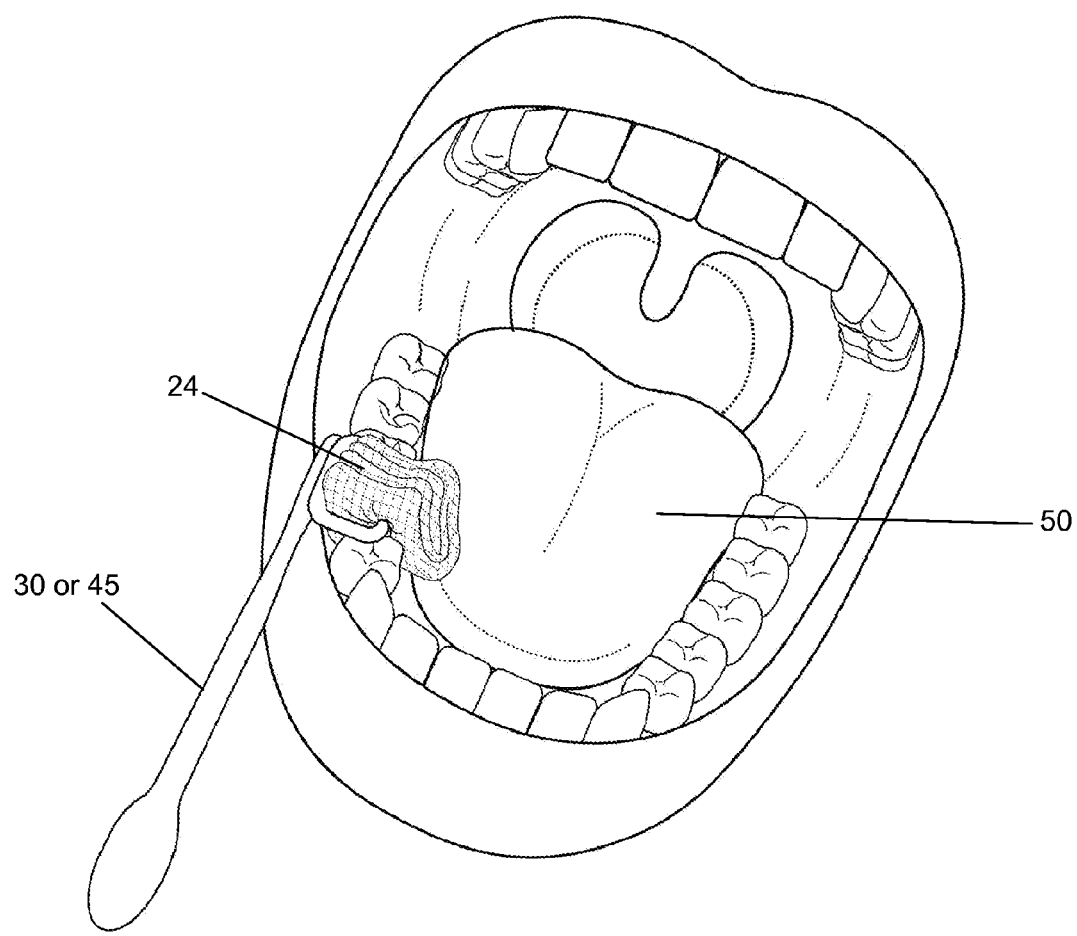
FIG. 11 shows a diagrammatical representation in perspective view of the post-surgical use of the embodiment types of the gauze pad holder illustrated in FIG. 5 or FIG. 6.
Figure 12:
FIG. 12 shows a diagrammatical representation in perspective view of the post-surgical use of any of the embodiment types of the gauze pad holder according to the instant invention.

In operational terms, gauze pad 24 is properly folded and assembled to the holder and after the surgical procedure has been performed, it is introduced and placed over the surgical area inside the patient's mouth using the handle section of the holder, thus avoiding introducing the fingers inside the oral cavity of the patient. FIGS. 10 and 11 illustrated the accommodation of the holder and gauze pad 24 in the patient's mouth 50. FIG. 10, illustrates the embodiment type 10 and 25 after an extraction or surgical procedure has been done in a molar tooth site. Alternatively, FIG. 11 shows the use of embodiment types 30 and 45 after a surgical procedure or extraction has been performed in a premolar tooth site. As indicated previously, each type of embodiment is ergonomically designed according to the anatomy of the oral cavity and the surroundings of the given surgical site. After the pad is accommodated on the pertinent surgical area, and the patient presses the gauze pad by closing the jaws as illustrated in FIG. 12, using embodiment 10 as an example, said pad should be maintained in the surgical area for about 30 minutes to maintain a dry field and allow the blood clot to form.

While the patient is using the herein described holder, the patient may secure said holder at any given time if necessary by holding the handle section, thus the patient may even talk carefully without the gauze pad being displaced from its holder. If necessary, the gauze pad 24 may be substituted by a new one by just repeating the described process.

Although the invention has been described and illustrated in detail, it is to be clearly understood that such description is for purposes of illustration and example and it is not intended to be taken by way of limitation. For instance, some sections of the gauze holder such as the elongated body, the handle and the holding unit may have alternatives shapes and/or configurations and still be within the spirit of the invention. Therefore, it is recognized that multiple variations exist, including both narrowing and broadening variations of the appended claims.

What it is claim is:

1. A holder, useful in holding a gauze pad in site after an intraoral surgical procedure, said holder comprising:
    a flat, oval-shaped handle section;
    a connecting section having a straight, elongated body, said connecting section comprising a first end connected to said flat, oval shaped handle section and a second end;
    a first C-shaped holding unit connected to the said second end of the connecting unit in an aligned or straight position to said flat oval shaped handle section;
    a flat, semi-rectangular supporting section comprising a right front corner and a right back corner, which is connected to and extending outwardly from the right side of said second end of the connecting section and perpendicularly positioned with reference to said handle section and said connecting section;
    a second C-shaped holding unit connected to the right front corner of the flat supporting section and located at the right side with reference to the first C-shaped holding unit and parallel to the handle section and to the connecting section;
    a single elongated-shaped internal cavity provided by the first C-shaped holding unit to the left side and the second C-shaped holding unit to the right side of said elongated cavity, said internal cavity located in a perpendicular position with reference to said handle section and said connecting section and;
    wherein a gauze pad may be held or secured in said cavity only by direct contact of the left and right sides of said gauze pad with the first and second holding units respectively, providing that the center of the gauze pad to be free of any physical interferences and wherein said gauze pad is held in a perpendicular position with reference to the handle section and said connecting section.

2. The holder as recited in claim 1, wherein the first and second C-shaped holding units further comprising a toothed internal surface.

3. The holder as recited in claim 2, wherein the handle section has a flat surface.

4. The holder of claim 3, wherein the elongated body of said elongated section is cylindrical.

5. The holder as recited in claim 1, wherein said holder is made of plastic.

6. The holder as recited in claim 1, wherein said holder is made of non-corrosive metal.

* * * * *